United States Patent [19]

Coughlin et al.

[11] 4,115,198

[45] Sep. 19, 1978

[54] METHOD OF IMMOBILIZATION OF BIOLOGICALLY ACTIVE ORGANIC SUBSTANCES INCLUDING ENZYMES

[76] Inventors: Robert W. Coughlin, 49 Storrs, Heights Rd., Conn. 06268; Marvin Charles, 622 N. 29 St., Allentown, Pa. 18104; Billy R. Allen, 2034 Dublin-Granville Rd., Columbus, Ohio 43229

[21] Appl. No.: 703,670

[22] Filed: Jul. 8, 1976

Related U.S. Application Data

[63] Continuation-in-part of Ser. No. 441,572, Feb. 11, 1974, abandoned.

[51] Int. Cl.² ............................................. C07G 7/02
[52] U.S. Cl. ......................................... 195/63; 195/68; 195/DIG. 11; 195/59; 195/60
[58] Field of Search ................... 195/63, 68, DIG. 11

[56] References Cited

U.S. PATENT DOCUMENTS

| 3,783,101 | 1/1974 | Tomb et al. | 195/63 |
| 3,912,593 | 10/1975 | Barker et al. | 195/63 |

*Primary Examiner*—Alvin E. Tanenholtz

[57] ABSTRACT

Insoluble supports are preactivated by precipitating thereon a hydrous metal oxide employing a hydrolysis reaction of a salt of said metal in the presence of said insoluble support. The resulting composite materials are employed as supports for immobilizing biologically active substances.

9 Claims, 1 Drawing Figure

METHOD OF IMMOBILIZATION OF BIOLOGICALLY ACTIVE ORGANIC SUBSTANCES INCLUDING ENZYMES

This application is a continuation in part of pending application Ser. No. 441,572 filed Feb. 11, 1974 and now abandoned.

BACKGROUND OF THE INVENTION

1. Field

This invention relates generally to immobilized, biologically active, nitrogen-containing, organic substances such as antigens, antibodies, antibiotics, enzymes and other proteins. The immobilized substances comprise insoluble carrier materials on which the said biologically active substances are bound. The binding may be by absorption, adsorption, chelation or other chemical coupling and the insoluble carrier materials may be organic or inorganic, metallic or non-metallic, porous or non-porous. As used herein the terms "immobile", "immobilized" and "immobilization", when applied to biologically active substances, refer to such biologically substances which have been rendered essentially insoluble by binding them to supporting carrier material in such a way that the resulting composite materials retain the original biological activity of the bound substances (such as enzymatic, coenzymatic, antibody or antigenic activity). More particularly, the present invention relates to the preparation of immobilized, biologically active, nitrogen-containing, organic substances (such as enzymic proteins) using supporting carrier materials formed by novel methods with the result that the biological activity of the immobilized biologically active substances is enhanced and displays a prolonged lifetime. According to the present invention, before attachment of the biologically active substance, the carrier material is treated by a process which causes a hydrous metal oxide to be deposited thereon; the metal-oxide-coated carrier material then is used as the support upon which the biologically active material is immobilized. Such carrier materials may be non-porous in which case the metal oxides are coated on their outer surfaces, or they may be porous in which case the metal oxide can be coated on the surfaces within the pores as well as on the outer surfaces.

2. Prior Art

Various methods of attachment of enzymic proteins to organic and inorganic insoluble carriers have been disclosed in U.S. Pat. No. 3,928,143. U.S. Pat. Nos. 3,556,945 and 3,519,538 respectively disclose immobilization of enzymic proteins on inorganic supports by adsorption and by chemical binding using silane coupling agents.

U.S. Pat. No. 3,783,101 discloses a more-water durable immobilized enzyme which comprises a thin, continuous layer of a metal oxide on the surface of a porous glass carrier, with the enzyme bonded to the metal-oxide layer through a silane coupling agent; the method of applying this coating as disclosed in the last mentioned patent amounts to merely contacting the porous glass with a metal solution followed by heating; in each such example shown in U.S. Pat. No. 3,783,101 the resulting initial immobilized enzymic activity in the cases of the metal-oxide-coated carriers or supports was less than, or about equal to, the activity of corresponding immobilized enzymes on the same carriers or supports which did not have the applied metal-oxide coating. The present invention discloses how to make an improved, immobilized biologically active substance (such as an enzyme) supported on metal-oxide-coated carriers in which the metal-oxide coating is applied by a novel method leading to immobilized substances which are unique to the method of coating the support with hydrous metal oxide, and which often show markedly enhanced specific biological activity (e.g. catalytic activity in the case of enzymes) as compared with the corresponding immobilized biological substances attached to the same carrier support material which has not been treated with a coating of metal oxide by our novel and unique method.

U.S. Pat. No. 3,841,969 discloses a process of preparing immobilized enzymes using supporting carriers prepared by reaction of the carrier material with an aqueous solution of a metal salt, drying and washing the resulting solid material, and then reacting this material with an enzyme so as to chelate the enzyme to the metal complex on the supporting material. In the present invention however a coating of metal oxide is formed by hydrolysis of a metal-salt solution; the metal oxide so formed is caused to deposit on the surface of the carrier material thereby conferring on the carrier material improved properties for immobilizing biologically active, nitrogen containing, organic substances such as enzymes and other proteins, by adsorption and by other immobilization techniques known in the art. The novel technique of the present invention differs from that of U.S. Pat. No. 3,841,969 in that our invention teaches the deposition on the carrier of an insoluble metal oxide formed according to the methods disclosed below.

U.S. Pat. No. 3,912,593 discloses water-insoluble, metal complexes of biologically active, nitrogen-containing, organic substances in which these complexes are formed by mixing the biologically active nitrogen-containing organic substances with a hydrous metal oxide capable of complexing with said substance. The present invention teaches how to prepare related substances by a novel process in which the metal oxide which complexes with said biologically active substance is coated by a novel method on a carrier material before contacting with the biologically active material.

The metal oxides employed in the present invention are those insoluble in aqueous solutions of about the pH whereat the respective enzyme displays maximum activity. Ordinarily this will be within a pH range of about 3 to 11. Any metal salt can accordingly be employed which will react to precipitate an oxide when the pH of its solution is adjusted to between about 3 to 11. Metals which are desirable in this regard are Ti, Zr, Sn, Fe, Al, V, Hf with Ti, Al, Sn and Zr preferred. Enzymes which can be immobilized according to the present invention include amyloglucosidase, lactase, glucose oxidase, invertase, trypsin, glucose isomerase, catalase, pronase, urease, lactate dehydrogenase, amino acid acylase, penicillin acylase, proteases and dextranase. Other biologically active substances which can be immobilized according to the present invention include antibodies, coenzymes such as nicotinamide adenine dinucleotide, antibiotics such as penicillin, gramicidin, lathumycin, neomycin, polymyxin, streptomycin, ampicillin and chloroamphenicol, and whole cells such as those of bakers' yeast and *Escherichia coli*.

Precipitation Of Hydrous Metal Oxides

In order to better adumbrate the operation of the present invention it is useful to consider the processes whereby insoluble metal oxides can be formed from corresponding aqueous solutions of the metal. Metal ions in aqueous solution generally are believed to exist as hydrated complexes in which a metal cation is associated with water molecules bound thereto; anions can also be bound as part of the complex hydrated ions. Representing the metal cation as $M^{m+}$ and anions which may also be present as $A^{a-}$ (whereby $m+$ represents the magnitude of the positive charge on the cation and $a-$ the magnitude of the negative charge on the anion) there then can exist in solution complex, hydrated ions of the form $[M_xA_y(H_2O)_z]^{(xm-ya)+}$ where $x$ is the number of metal cations, $y$ the number of anions and $Z$ the number of water molecules making up the complex. These complexes can be non ionic (neutral) if $xm = ya$; otherwise they are positively charged if $xm > ya$ (cationic complexes) or negatively charged if $xm < ya$ (anionic complexes). It is generally believed that the water molecules in these complexes are oriented with the negatively charged portion of the water molecule (the oxygen atom) close to the positively charged metal cation whereas the protons of the water molecule will tend to be repelled from the positively charged metal ion in the complex; in fact a proton of an associated water molecule in a positively charged complex can dissociate therefrom leaving behind a negatively charged hydroxyl ion within the complex as represented by the equation:

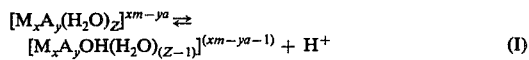

(I)

Thus the process of losing one proton ($H^+$ion) causes the net positive charge on the complex to decrease by unity. Similarly, a negatively charged complex (shown in the next equation as containing "$w$" hydroxyl ions) can absorb protons thereby converting a constituent hydroxyl ion to a water molecule with a result that the net negative charge on the complex decreases by unity:

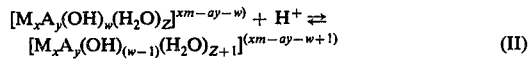

(II)

Alternatively, the exchange of protons may involve an anion, $A^{a-}$, or a neutral acid molecule, HA, within the complex as represented by the following two equations:

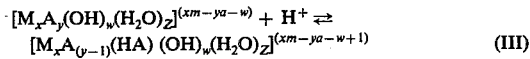

(III)

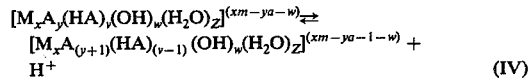

(IV)

According to the foregoing equations, complex metallic species in solution may gain or lose protons with an associated gain or loss of positive charge. By such gain or loss of protons a positively charged or a negatively charged complex may be converted to a neutral or near neutral complex; such neutral or near-neutral complexes are believed to be the precursers of precipitates; so long as the complexes all retain the same type of charge they will repel each other according to Coulomb's law but neutral complexes may associate, polymerize, and eventually grow sufficiently large to attain colloidal size; the colloidal particles may deposit on surfaces or may coagulate and form precipitates.

It should be noted that according to the theory described above, the precipitation of metals from their solutions by hydrolysis or by association or dissociation of protons with or from charged complexes of the metal in solution, will result in solid oxides which are hydrated and which will often also contain anions within their structure. Examples are hydrous zirconium and hafnium oxychlorides precipitated from aqueous solutions of their respective chlorides. Such hydrated oxides which are formed by precipitation and frequently contain other constituents (often in non-stoichiometric proportions) are meant to be encompassed when referring herein to hydrous metal oxides.

The theory of ion formation outlined above remains only a theory and is poorly understood — especially details as to the exact compositions of hydrous complex metal oxides and the complex aqueous ions which are their precursors. Equations I through IV above are consistent, however, with the fact that hydrous complex metal oxides can be precipitated from solutions by neutralization; i.e. by the addition of base to acidic solutions in order to cause reactions such as I and IV above to proceed from left to right or by the addition of acid to basic solutions to cause reactions such as II and III above to proceed from left to right. Well known examples are the precipitation of hydrous aluminum oxides and silicon oxides by adding acid to basic aluminate or silicate solutions as well as the precipitation of hydrous tin and titanium oxides by adding base to acidic solutions of tin chloride, tin sulfate, titanium chloride or titanium sulfate. It is also possible to precipitate hydrous metal oxides from such solutions by diluting such concentrated solutions by mixing a more concentrated with a less concentrated such solution. According to the theory outlined above precipitation by such dilution may be thought of as the displacement of OH ions from negatively charged hydroxy complex ions by water molecules or, in the case of positively charged complex ions, as the incorporation of additional water into the structure of the complex ion which can then decrease in positive charge by losing protons from the added water molecules. Hydrolysis of a solution of a metal salt by dilution may also be thought of as a kind of neutralization in those cases where the starting solution is either acidic or basic. Dilution of such a solution will tend to change its pH in the direction of neutrality and, therefore, may be understood as a form of neutralization.

It should be mentioned that heating can play a very important role in precipitating hydrous metal oxides from solutions. After neutralization by addition of acid or base to a solution of a metal compound, or after dilution of such a solution, the thermodynamic conditions for precipitation of the respective oxide may be present but the rate of such precipitation, or the rate of certain required precurser reactions, may be so slow that the solution appears to be in a metastable state and no discernable precipitation may be evident. In such cases it will frequently be practical and convenient to bring about the required precipitation by heating the mixture. Heating may play yet another role in promoting precipitation of hydrous metal oxides by causing a gaseous reaction product to evolve from the mixture thereby permitting the precipitation to continue or to occur to an extent greater than in an unheated case; for example when chlorides of transition metals are hydrolyzed it appears that heating tends to allow the reaction to occur to a greater extent by expelling HCl, a gaseous reaction product, from the mixture. Thus it will be recognized that, although it appears that heating will not be a necessary processing step in the method of this invention, nevertheless heating will frequently be a desirable and useful step.

DESCRIPTION OF PREFERRED EMBODIMENTS

Figure 1:
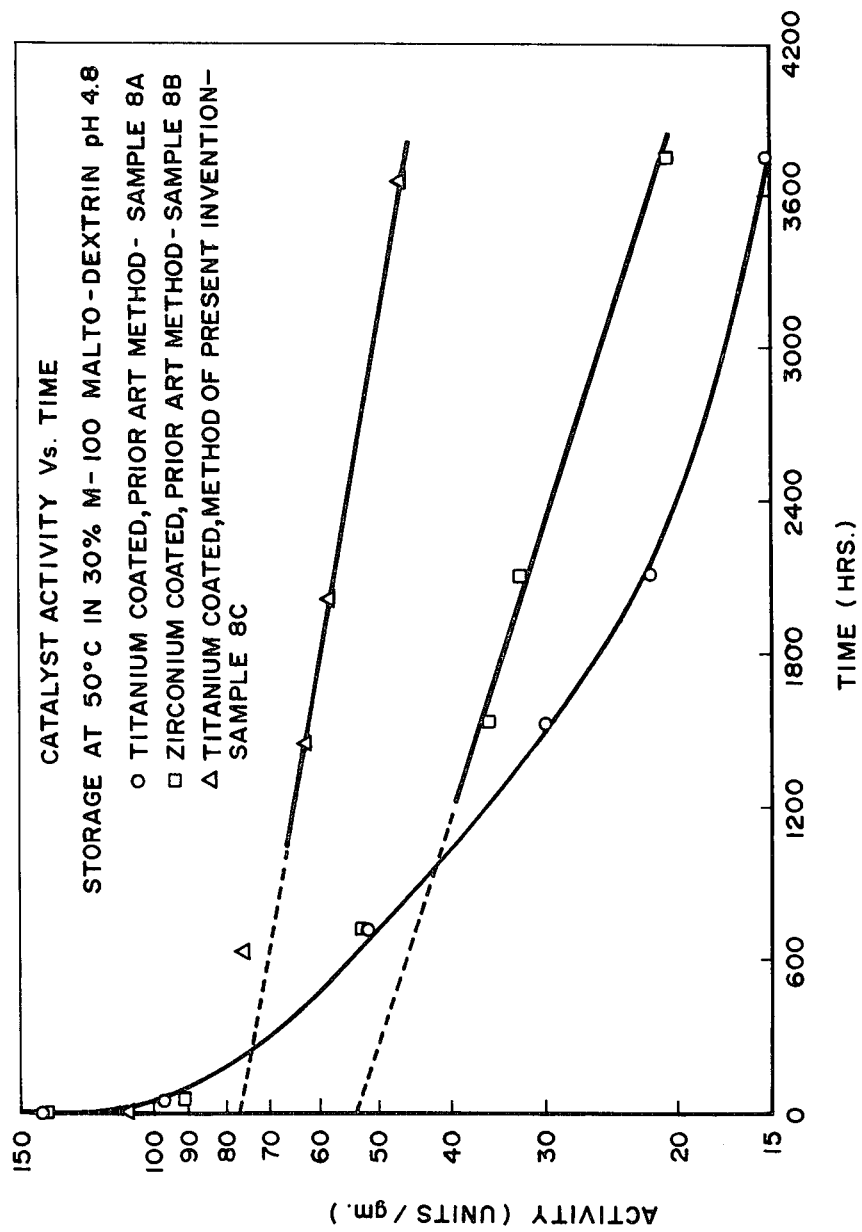

We have now discovered that the formation of hydrous metal oxides as described above but conducted in the presence of insoluble base carrier particles causes a tenaciously adhering layer of the hydrous metal oxide to be deposited on the surface of the insoluble carrier particles and that the resulting composite materials have very favorable properties when employed as supporting carriers for biologically active nitrogen-containing organic substances such as antigens, antibodies, antibiotics, enzymes and other proteins. In other words, insoluble particles coated with layers of hydrous metal oxides made by the method of our invention act as supports or carriers which show superior properties for the immobilization of such biologically active substances.

Such superior properties are associated with the method whereby the insoluble base support particles are present in the mixture wherein the formation of the hydrous metal oxides occurs. We have noted by microscopic observation that in this process a porous layer of hydrous metal oxide forms on the outside of a non-porous carrier particle such as stainless steel of particle size averaging about 150 micrometers and that the specific surface area of the resulting composite solid support material is frequently thereby increased by a factor as large as ten. Presumably a similar deposition of hydrous metal oxide also takes place within the pores of porous particles but, of course, ordinary microscopic techniques are of no avail for observing such depositions. We have found that, in the case of porous base particles, it is often desirable to limit the extent of deposition of hydrous metal oxide so as not to unduly restrict access to the pores for the biologically active substances to be immobilized subsequently thereon.

The deposition of high-surface-area, hydrous metal oxides on base carrier particles is unique to the method of preparation in that such deposits appear to arise from the interaction of the base carrier particles with colloidal hydrous metal oxides formed during the precipitation process. Such coatings do not form, for example, on the base carrier particles by merely contacting them with the solution of the metal salt or even with a slurry of already precipitated hydrous metal oxide. The fact that the superior coating of metal oxide is formed on, and tenaciously adheres to the base carrier particles only when they are present during the precipitation of the metal oxides and in contact with the reaction mixture is consistent with the disclosures of Blumenfeld in U.S. Pat. No. 1,795,467 and Mecklenburg in U.S. Pat. No. 1,758,528. In the latter two patents the supposed mechanism of precipitation is discussed as involving the formation of colloidal particles of the hydrous metal oxide as an early or primary step in the process of precipitation from solution. It will be clear from the aforecited U.S. Pat. Nos. 1.758,528 and 1,795,467 as well as U.S. Pat. No. 2,369,468, and from the theoretical discussion above, that precipitation of hydrous metal oxide from aqueous solutions of their salts can be accomplished by heating, by diluting and by neutralizing with either an acid or a base, or by a combination of several of these methods.

According to the present invention a hydrous metal oxide is precipitated from a solution of the said metal upon an insoluble base carrier material suspended therein. The resulting composite material is then used as a support for immobilizing nitrogen-containing, biologically-active, organic substances. It appears that any suitable insoluble particulate material, organic or inorganic, metallic or non-metallic, can be coated with hydrous metal oxide in this way. The method of coating by precipitation of the hydrous metal oxide from a solution of the metal in which the insoluble base carrier material is suspended is necessary to obtain the improved results of the present invention. Merely mixing base carrier material with already precipitated hydrous metal oxide does not result in composite materials upon which enzymes can be immobilized simply and conveniently to form immobilized enzymes of improved properties. Neither does mere contact between the base carrier particles and the metal solution. Apparently, by precipitation of the hydrous metal oxide in the presence of the insoluble base support material colloidal particles of the former are caused to adhere intimately, tenaciously and evenly upon particles of the latter, thereby forming a composite material having improved properties. For example, the resulting material will have the approximate size and density of the insoluble base support material, but usually a greatly enhanced specific surface area, and in particular, the resulting composite material will show a superior ability to bind biologically active, nitrogen-containing organic substances, presumably due to the coating of hydrous metal oxide. It is not well understood why or how such hydrous metal oxides have superior ability to bind such biologically active materials but the mechanism therefor has been attributed to chelation in U.S. Pat. No. 3,912,593.

It should be emphasized that the enzyme supports and the resulting immobilized enzymes themselves are articles that are unique to the method of preparation. In this regard the fact that the mere mixing together of metal oxide particles with the support, whether water is present or not, does not produce a support or a resulting immobilized enzyme with the properties that are realized by precipitation of such oxides from solution on to the supporting materials; this result appears to be associated with the colloidal nature of the precipitate particles formed earliest — when a supporting material is present in the same mixture with such early-formed colloidal particles the latter tend to tenaciously adhere to the support and, because of their small size, to form a porous, highly reactive deposit of high specific surface area on the carrier materials. As evident from the Examples to follow the nature and properties of such carriers activated with hydrous metal oxide according to the present invention are sensitive to the reaction time and to subsequent drying and this is in accord with their unique nature which does not appear to be capable of full description except in terms of the method of their manufacture.

EXAMPLES

The present invention is illustrated by the following examples which are intended to show preferred embodiments but are not intended to limit the scope of the invention. The insoluble support materials that are employed are illustrated by the following table:

| Table of Support Materials Used In The Examples | | | |
| --- | --- | --- | --- |
| | Porous Supports Materials | | |
| Supplier | Material | Surface Area (m$^2$/gm.) | Particle Size ($\mu$) |

Table of Support Materials Used In The Examples -continued

| Supplier | Material | Surface Area (m²/gm.) | Particle Size (μ) |
| --- | --- | --- | --- |
| Carborundum Co. | SAEHS-33(Al₂O₃) | 4.0 | −250 + 149 |
| Carborundum Co. | SAEHS-33(Al₂O₃) | 8.0 | −177 + 105 |
| Houdry Chemical Co. | Catalyst No. 9C79-12C(SiO₂) | (unknown) | −250 + 149 |

Semi or Non-Porous Supports Materials

| Supplier | Material | Surface Area (m²/gm.) | Particle Size (μ) |
| --- | --- | --- | --- |
| Glidden Metals Co. | 316-L-Si Pre-alloyed stainless steel powder | 0.19 | −149 + 53 |
| International Nickel Co. | Sinter 90 (Ni-NiO) | (unknown) | −420 + 180 |
| Harshaw Chemical Co. | Ni-1000 P (NiAl) | (unknown) | −100 + 50 |

EXAMPLE 1

To a reaction flask containing 10.0 gm. of Carborundum Co. (SAEHS-33 4m²/gm.) alumina and 62.5 ml. of chilled water, 6.3 ml. of titanic chloride reagent (liquid TiCl₄ purchased from the Fisher Scientific Co.) was slowly added with vigorous stirring. The reaction flask was partially immersed in an ice bath to remove the heat generated by the addition of the chloride solution. The flask was then removed from the ice bath, heated to 80° C., and held at that temperature for 1.0 hour. The resulting titanium oxide-coated alumina support was then removed from the flask and washed thoroughly with tap water until a clear rinse was obtained. The coated alumina was then dried overnight at 110° C.

A solution of commercial amyloglucosidase (Wallerstein Amigase DM-200) was prepared by adding 1.0 gm. (dry wt.) of the enzyme powder to 50 ml. of deionized water. Samples of both titanium oxide coated and non-coated (untreated) alumina (5.0 gm. each) were contacted at 0°-5° C. for 18 hours with 25 ml. of the enzyme solution. The alumina samples were then washed four to six times with deionized water before being assayed for enzyme activity.

Amyloglucosidase activity of the immobilized derivatives was determined in the following manner: A small amount of the immobilized catalyst (0.1000 to 0.4000 gm.) was added to 10.0 ml. of thermally equilibrated substrate (10% wt./vol., Maltrin M-250 "Malto-Dextrin" in deionized water, pH 5.0). Agitation was provided by a reciprocating shaker bath operated at about 125 strokes per minute. After a predetermined period of time, a 1.0 ml. aliquot of the assay solution was added to 9.0 ml. of 0.018 F sodium carbonate — 0.002 F sodium bicarbonate buffer, pH 10.5. The glucose concentration was then analyzed using a Yellow Springs Instrument Co. Model 23A Glucose Analyzer. Care was taken to adjust the reaction time and the amount of immobilized enzyme to limit the starch conversion to 20% or less. Amyloglucosidase activity was expressed as Units per gram of support (dry wt.). One Unit of activity represents the production of 1.0 μ mole of glucose per minute at 37° C.

Results

| Sample No. | Suppport Material | Immobilized Activity (Units/gm.) | Binding Efficiency |
| --- | --- | --- | --- |
| 1A | Titanium oxide coated Carborundum (4 m²/gm.) Alumina (SAEHS-33) | 88. | 24% |
| 1B | Non-coated Carborundum (4 m²/gm.) Alumina (SAEHS-33) | 26. | 7% |

Note: Binding efficiency equals the percentage of the soluble activity offered for binding which is recovered as immobilized activity.

EXAMPLE 2

Samples of titanium oxide coated (Carborundum Co., 4 m²/gm.) alumina were prepared as described in Example 1 except that the liquid TiCl₄ reagent was added in differing proportions to the support materials slurried in water. The reaction time defined as the length of the reaction period at 80° C. was also varied. The resulting coated samples were contacted at 0°-5° C. for 18 hours with solutions of equal concentrations of amyloglucosidase and then washed with deionized water before being assayed as in Example 1. Enzyme activities were determined in a similar manner to that described in Example 1.

Results

| Sample No. | Water-to-Alumina Ratio (ml./gm.) | Volume Proportion of TiCl₄ liquid reagent to water (ml/ml) | Reaction Time (min.) | Immobilized Activity (Units/gm.) |
| --- | --- | --- | --- | --- |
| 2A | 6.1 | 0.1 | 60 | 88. |
| 2B | 2.0 | 0.1 | 60 | 66. |
| 2C | 2.0 | 0.1 | 15 | 41. |
| 2D | 6.1 | 0.2 | 60 | 76. |
| 2E | 6.1 | 0.2 | 180 | 51. |

Note: Support - Carborundum Co. (4m²/gm.) alumina

EXAMPLE 3

The same coating procedure as in Example 1 was used except that part of the coated Carborundum Co. (4 m²/gm.) alumina was not dried before being contacted with the amyloglucosidase solution. Another portion of the coated alumina was dried at 110° C. for 18 hours and then contacted with the enzyme solution as in Example 1. The amyloglucosidase activity of the immobilized derivatives was also determined as in Example 1.

Results

| Support Material | Immobilized Activity (Units/gm) |
| --- | --- |
| Titanium oxide Coated Alumina (Dried at 110° C) | 80. |
| Titanium oxide Coated Alumina (Not Dried) | 36. |

Note: Support - Carborundum Co. (4 m²/gm.) Alumina

EXAMPLE 4

Porous oxide-coated supports were prepared using the same procedure as in Example 1 except that the ratio of water-to-support material was varied whereas the volumetric ratio of TiCl₄ reagent to water was held at 0.1 ml./ml. All other procedures and conditions were the same. Immobilized amyloglucosidase was prepared using both coated and non-coated supports by contacting each support with a solution of the enzyme as in Example 1. The immobilized activities were also determined as in Example 1.

| Sample No. | Support Material | Water-to-Support Ratio (ml/gm) | Immobilized Activity | Binding Efficiency (%) |
|---|---|---|---|---|
| 4A | Titanium oxide coated Carborundum Co.(8m²/gm.)Alumina | 2.0 | 160. | 43 |
| 4B | Non-coated Carborundum Co. (8 m²/gm) Alumina | — | 26. | 7 |
| 4C | Titanium oxide coated Houdry Silica | 6.1 | 133. | 36 |
| 4D | Non-coated Houdry Silica | — | None | — |
| 4E | Titanium oxide coated Harshaw Nickel/Aluminum | 2.0 | 16. | 4 |
| 4F | Non-coated Harshaw Nickel/Aluminum | — | 1.4 | 0.4 |

Binding efficiency equals the percentage of the soluble activity offered for binding recovered as immobilized activity.

EXAMPLE 5

The same procedure as in Example 1 was used except that other reagents were added to the water slurry of support material as follows:

| Reagent | Proportion of Reagent Added to Water Slurry |
|---|---|
| $SnCl_3$—$H_2O$ | 0.1 gm regent/ml $H_2O$ |
| $AlCl_3$ | 0.1 gm reagent/ml $H_2O$ |
| 20% $TiCl_3$ in $H_2O$ | 1 ml reagent/ml $H_2O$ |

Different proportions of water-to-alumina (the only support used in this example) and different reaction times (defined as the length of the reaction period at 80° C.) were tested. Immobilized amyloglucosidase derivatives were prepared by contacting 5.0 gm. of each oxide coated support with 25.0 ml. of enzyme solution (20 mg./ml. Wallerstein Amigase DM-200 in deionized water) for 18 hours at 0°-5° C. After several washing cycles with deionized water, the immobilized activity of each sample was determined as in Example 1.

| Sample No. | Salt | Water-to-Alumina Ratio (ml/gm) | Reaction Time (min) | Immobilized Activity (Units/gm.) |
|---|---|---|---|---|
| 5A | $SnCl_2 . H_2O$ | 2.0 | 30 | 103. |
| 5B | $SnCl_2 . H_2O$ | 2.0 | 60 | 89. |
| 5C | $SnCl_2 . H_2O$ | 4.0 | 30 | 83. |
| 5D | $SnCl_2 . H_2O$ | 4.0 | 60 | 85. |
| 5E | $AlCl_3$ | 2.0 | 30 | 121. |
| 5F | $AlCl_3$ | 2.0 | 60 | 109. |
| 5G | $AlCl_3$ | 4.0 | 30 | 118. |
| 5H | $AlCl_3$ | 4.0 | 60 | 121. |
| 5I | $TiCl_3$ | 2.0 | 30 | 68. |
| 5J | $TiCl_3$ | 2.0 | 60 | 65. |
| 5K | $TiCl_3$ | 4.0 | 30 | 64. |
| 5L | $TiCl_3$ | 4.0 | 60 | 61. |
| 5M | (Non-coated) | — | — | 26. |

Note: Support - Carborundum Co. (8 m²/gm.) alumina

EXAMPLE 6

Samples of non-porous, Glidden 316 stainless steel powder were coated with hydrous titanium oxide using the same procedure as in Example 1 (with 0.1 ml. of $TiCl_4$ reagent per ml. $H_2O$) except that different proportions of water-to-steel, different reaction temperatures, and different reaction times (defined as the length of the reaction period at the specified temperature) were used.

The coated supports and a sample of non-coated stainless steel were contacted at 0°-5° C. for 18 hours with amyloglucosidase solutions containing 20 mg./ml. of Wallerstein Amigase DM-200 in deionized water. The stainless steel samples were then subjected to four to six washings with deionized water before being assayed as given in Example 1.

| Sample No. | Water-to-Steel Ratio (ml./gm.) | Reaction Temperature (° C) | Reaction Time (min.) | Immobilized Enzymatic Activity (Units/gm.) |
|---|---|---|---|---|
| 1 | 6.1 | 70 – 80 | 30 | 8.2 |
| 2 | 6.1 | 70 – 80 | 60 | 9.4 |
| 3 | 2.0 | 70 – 80 | 30 | 5.2 |
| 4 | 2.0 | 70 – 80 | 60 | 12.4 |
| 5 | 2.0 | 80 | 120 | 23.5 |
| 6 | 2.0 | 80 | 180 | 17.9 |
| 7 | 6.1 | 50 – 60 | 30 | 1.0 |
| 8 | 6.1 | 50 – 60 | 60 | 1.2 |
| 9 | 2.0 | 50 – 60 | 30 | 0.45 |
| 10 | 2.0 | 50 – 60 | 60 | 0.73 |
| 11 | Non-coated | — | — | None |

Note: Support - Glidden Metals Co. 316-L-Si Prealloyed Stainless Steel.

EXAMPLE 7

The Ni/NiO (Sinter 90) support from the International Nickel Company was activated using $TiCl_4$ as in Example 1. The resulting support coated with hydrous titanium oxide was contacted with a buffered solution of lactase (lactase-LP supplied by the Wallerstein Corp.) in the following proportions: 1 gm. activated Sinter 90, 3 ml. citrate-phosphate buffer (pH=4.0) and 24 mg. of the lactase. After 12 hours of contact at 5° C. the particles were separated and washed with buffer solution whereupon they displayed an enzymatic activity of 100–300 lactase units per gm. Here a lactase unit is defined as that enzymatic activity which will produce $3.8 \times 10^{-8}$ moles of glucose per minute by hydrolysis of lactose at pH = 3.5, temperature = 30° C. and initial lactose concentration of 20% by weight. Glucose concentration in this Example 7 was measured using the Glucostat analysis kit supplied by Worthington Biochemical Corp. Similar results were also obtained by applying essentially the same procedure but starting with stainless steel (Glidden Corp. 316 stainless steel) as the supporting material.

EXAMPLE 8

For comparison with the present invention, samples of the Carborundum Co. (8 m²/gm.) SAEHS-33 alumina were coated with oxides of titanium and zirconium using the prior art method of Tomb et al according to the teachings of U.S. Pat. No. 3,783,101. Following the prior-art method 15 gm. of alumina was placed in a solution of 3 ml. of $TiCl_4$ reagent in 30 ml. of water, contained in a Petri dish. The dish was placed in a vacuum desicator for approximately 30 minutes and then dried overnight in an oven at 150° C. The catalyst prepared (as described below) from the resulting coated support material is referred to below as sample 8A. A second sample (sample 8B) was prepared using the same prior-art procedure except that 45.0 ml. of water were used and 4.5 gm. of $ZrOCl_2$ were substituted for the titanic chloride. After the drying period, both samples 8A & 8B were placed in a tube furnace and slowly heated over a 3.0 hour period to 500° C. The temperature was maintained at 500° C. for an additional 3.0 hours after which the samples were slowly cooled to 100° C. and placed in a drying oven (at 100° C.) for storage. All of the foregoing steps are taught by U.S. Pat. No. 3,783,101.

Samples (8A & 8B) of both the titanium-and zirconium-coated alumina (5.0 gm. each and each prepared according to the prior-art method as outlined above) were then contacted at 0°–5° C. for 18 hours with 25.0 ml. of an unbuffered solution containing 20.0 mg./ml. of the Wallerstein amyloglucosidase. In order to compare the prior art method and catalyst, a third catalyst sample (8C) was prepared according to the Example 1 method using alumina which had been coated with titanium oxide as described in Example 1 above. After contacting with enzyme solutions, each of the three samples was washed with deionized water and contacted for 3.0 hours (at 5° C.) with a 2.5% solution of glutaraldehyde in deionized water (pH 7.0). After crosslinking by this glutaraldehyde treatment, the samples were washed repeatedly with deionized water before being assayed according to the procedure of Example 1. The results of the initial assays showed that the prior-art catalysts had somewhat greater initial enzymatic activity as shown in the following table.

| Sample No. | Support | Initial Immobilized Activity (Units/gm.) |
| --- | --- | --- |
| 8A | Titanium Coated + Calcining (prior art method) | 140 |
| 8B | Zirconium Coated + Calcining (prior art method) | 137 |
| 8C | Titanium Coated (Present Invention Method) | 117 |

The long-term stability of the enzymic catalyst (8C) prepared according to the present invention was superior, however, to corresponding catalysts (8A & 8B) prepared by the prior-art method as shown in FIG. 1. Accordingly sample 8B showed an apparent half life of about 2750 hours; sample 8A was very unstable and displayed a much shorter half life; sample 8C prepared according to the present invention had a half life of about 4950 hrs. Stability evaluation was as follows: the samples were stored at 50° C. in 45 ml. of substrate (30% M-100 (10 D.E.) Malto-Dextrin, pH 4.8). Periodically, they were washed with deionized water, assayed, and again stored in fresh substrate. Both catalyst samples (8A & 8B) prepared by the prior-art method were significantly less stable than the sample (8C) prepared according to the instant invention as taught in Example 1. This result shows that not only is our novel method superior to the prior-art method but that our resulting product is also novel in that it has new and improved stability properties which undoubtedly arise from the new method itself and the colloidal properties of the in situ formed precipitate by which the support materials are coated.

EXAMPLE 9

A sample of Carborundum (8 $m^2$/gm. SAEHS-33) alumina was treated using the same procedure as in Example 1 except that the proportion of water to alumina was 2.0 ml./gm. and the water was not chilled before or during the addition of the titanic chloride (the proportion of $TiCl_4$ to $H_2O$ was 0.1 ml./ml. as in Example 1). All other procedures were as given in Example 1. The immobilized amyloglucosidase activity obtained with the coated alumina was 97.2 Units/gm. This example is given to show that chilling the water before or during the addition of the metal salts reagent is not a necessary step in the method of the present invention. We have found such chilling to be desirable when much heat is liberated as when certain metal salt reagents react with the water slurry; e.g. the chilling is convenient to prevent boiling and spattering of the metal salt reagent.

In the foregoing examples no precipitation was observed at the dilution step when the metal salt reagent was added to the slurry of support material-in-water. Not until the resulting slurry was heated (preferred range about 50°–95° C.) did a fine colloidal precipitate form that adhered tenaciously to the glass vessels employed as well as the support material; only a small fraction of this colloidal precipitate appeared to adhere to the support materials, presumably forming a very thin coating thereon. However the heating step is not always necessary; $SiCl_4$, for example, forms a precipitate immediately upon addition to water. Although heating appears to be necessary in the foregoing examples to accelerate or cause the completion of the precipitation reaction, it is clear that heating will not always be necessary (as with $SiCl_4$) to form a colloidal precipitate, depending on the nature of the metal salt reagent, on the proportions of water to such reagent and also depending on whether acidic or basic reagents are also employed to cause the precipitation.

What is claimed is:

1. A method of preparing water-insoluble enzymes comprising the steps:
    (a) precipitating a hydrous metal oxide from a solution of a salt of said metal in the presence of an insoluble support material so as to form a coating of the said oxide on the said support,
    (b) washing the composite support material resulting from step a,
    (c) contacting the composite support material resulting from step b with a solution of an enzyme so as to immobilize said enzyme on said support material.

2. The method of claim 1 wherein the mixture resulting from steps a and b is heated after the washing step b.

3. The method of claim 2 wherein the precipitation is accomplished by hydrolysis of a salt of the said metal.

4. The method of claim 3 wherein the said metal is chosen from the group consisting of Ti, Sn, Zr, Al, Fe, V and Hf.

5. Water-insoluble enzymes produced by the method of claim 2.

6. Water-insoluble enzymes produced by the method of claim 3.

7. Water-insoluble enzymes produced by the method of claim 4.

8. Water-insoluble enzymes produced by the method of claim 1.

9. Water-insoluble enzymes according to claim 8 wherein the enzymes are chosen from the group consisting of lactase, amyloglucosidase and glucose isomerase.

* * * * *